(12) United States Patent
Nöcker et al.

(10) Patent No.: US 11,324,685 B2
(45) Date of Patent: May 10, 2022

(54) PROCESS FOR TREATING HAIR

(71) Applicant: KAO GERMANY GMBH, Darmstadt (DE)

(72) Inventors: Bernd Nöcker, Darmstadt (DE); Steven Breakspear, Darmstadt (DE); Niu Jian, Darmstadt (DE)

(73) Assignee: KAO GERMANY GMBH, Darmstadt (DE)

(*) Notice: Subject to any disclaimer, the term of this patent is extended or adjusted under 35 U.S.C. 154(b) by 468 days.

(21) Appl. No.: 16/307,348

(22) PCT Filed: Jun. 1, 2017

(86) PCT No.: PCT/EP2017/063323
§ 371 (c)(1),
(2) Date: Dec. 5, 2018

(87) PCT Pub. No.: WO2017/211683
PCT Pub. Date: Dec. 14, 2017

(65) Prior Publication Data
US 2019/0133909 A1     May 9, 2019

(30) Foreign Application Priority Data

Jun. 7, 2016 (EP) .................................... 16173310

(51) Int. Cl.
| | | |
|---|---|---|
| *A61K 8/49* | (2006.01) | |
| *A61Q 5/04* | (2006.01) | |
| *A61Q 5/06* | (2006.01) | |
| *A45D 7/04* | (2006.01) | |

(52) U.S. Cl.
CPC ................. *A61K 8/498* (2013.01); *A45D 7/04* (2013.01); *A61Q 5/04* (2013.01); *A61Q 5/06* (2013.01)

(58) Field of Classification Search
None
See application file for complete search history.

(56) References Cited

U.S. PATENT DOCUMENTS

| | | | |
|---|---|---|---|
| 4,452,261 A | 6/1984 | Bresak et al. | |
| 2003/0180277 A1* | 9/2003 | Hoppe | A61Q 7/00 424/94.1 |
| 2008/0185014 A1* | 8/2008 | Campain | A45D 7/06 132/210 |
| 2008/0311050 A1 | 12/2008 | Lendlein et al. | |
| 2013/0118520 A1 | 5/2013 | Mannozzi | |
| 2013/0233332 A1* | 9/2013 | Khenniche | A61Q 5/12 132/202 |
| 2013/0298933 A1 | 11/2013 | Malle et al. | |
| 2014/0335038 A1 | 11/2014 | Bhogal et al. | |
| 2016/0073756 A1 | 5/2016 | Mannozzi | |

FOREIGN PATENT DOCUMENTS

| | | |
|---|---|---|
| EP | 2 029 236 A1 | 3/2009 |
| WO | 2005/011626 A1 | 2/2005 |
| WO | 2011/039098 A1 | 4/2011 |
| WO | 2012/010351 A2 | 1/2012 |

OTHER PUBLICATIONS

Mintel, Database GNPD, "Hot Curls Perfector", retrieved from http://www.gnpd.com, Jul. 1, 2012.
Mintel, Database GNPD, "Flat Iron Protection Shine Mist Spray", retrieved from http://www.gnpd.com, Mar. 2013.
Babyliss, retrieved from http://www.babyliss.de/produkte/haarpflege/heislockenwickler/3021egnpd.com, Apr. 24, 2016.
International Search Report dated Jul. 18, 2017, dated Sep. 27, 2018.

\* cited by examiner

*Primary Examiner* — Nicole P Babson
(74) *Attorney, Agent, or Firm* — Norris McLaughlin, P.A.

(57) ABSTRACT

The present invention relates to a process for treating hair wherein the hair is semi permanently shaped and subsequently reshaped with the application of an aqueous composition comprising catechin and/or resorcinol and their derivatives.

15 Claims, No Drawings

PROCESS FOR TREATING HAIR

This application is the U.S. National Stage of International Application No. PCT/EP2017/063323, filed Jun. 1, 2017, which claims foreign priority benefit under 35 U.S.C. § 119 of European Application No. 16173310.0 filed Jun. 7, 2016 the disclosures of which are incorporated herein by reference.

The present invention relates to a process for treating hair wherein the hair is semi permanently shaped and subsequently reshaped with the application of an aqueous composition.

Semi-permanent hair shaping has recently become widely used, especially for hair straightening with aqueous compositions comprising non reducing compounds. The hair straightened in this way holds its straightened shape for several hair washes to several months. However, this process does not allow consumers to have their hair subsequently adjusted into variable shapes and especially giving hair curls in order to increase the volume is not possible. In other words, these processes do not give any flexibility in subsequent hair shaping.

Well known traditional processes based on the use of reductive and oxidative compositions produces solid hair shapes which may not be changed without using additional chemical processes. Furthermore, these processes do damage hair which results in loss of hair natural properties, especially its strength and elasticity.

Resorcinol and its derivatives have been suggested for straightening hair in EP 2029236. The document focuses solely on straightening and does not provide any evidence of curling and flexible hair shaping.

The well-established glyoxylic acid based semi-permanent straighteners, such as in WO2012/010351, uses straightening iron and provides relatively long lasting straightening. Here again, there is no flexibility given of reshaping hair.

WO 2011/039098 discloses permanent styling process using two thiosiloxanes for providing long lasting styling benefits. According to the process, oxidative fixative is needed with the aid of hydrogen peroxide.

WO 2005/011626 discloses method of restyling hair using very hydrophobic, almost non-aqueous compositions. Hair is arranged in a defined shape and fixed physically with the composition. The effect is not long lasting.

The above summarized processes provide certain level of hair shaping which may be effective in the given shape but does not provide, or in some cases even make impossible, to change the hair style without using additional chemical process. The use of additional chemical processes on already chemically processed hair is harmful as it further damages hair which results in loss of hair natural properties.

The aim of the present invention is to find a new process for flexibly and durably shaping hair, especially curling and straightening semi permanently, and which makes change of hair shape possible without using any extensive chemical processes.

The present inventors have unexpectedly found that treating hair with a composition comprising one or more compounds selected from catechine, resorcinol and its derivatives which does not comprise any alpha hydroxy acid makes possible obtaining durable larger curls and gives possibility to change hair style flexibly from straight to curly solely with the aid of hair styling tools such as irons, brushes, etc., and without using any additional chemical treatment process.

Accordingly, the first object of the present invention is a process for treating hair comprising the following steps:
a—optionally cleansing hair,
b—optionally drying the hair,
c—applying an aqueous composition onto hair comprising one or more compounds of the general structure

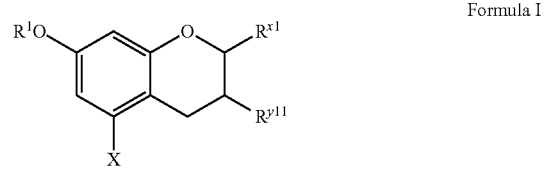

Formula I wherein
$R^1$ represents a hydrogen atom or a methyl group,
X represents a hydrogen atom, a hydroxy group, or a methoxy group,
$R^{x1}$ represents an aromatic hydrocarbon group, which is optionally substituted with up to three hydroxy groups or methoxy groups and which optionally forms a condensed ring with 1,3-dioxolane, and
$R^{y11}$ represents a hydroxy group, a methoxy group, or an aromatic hydrocarbon group, which is optionally substituted with up to three hydroxy groups or methoxy groups and which optionally forms a condensed ring with 1,3-dioxolane, or an arylcarbonyloxy group or aralkylcarbonyloxy group, which is optionally substituted with up to three hydroxy groups or methoxy groups,
and/or
one or more compounds of the general structure

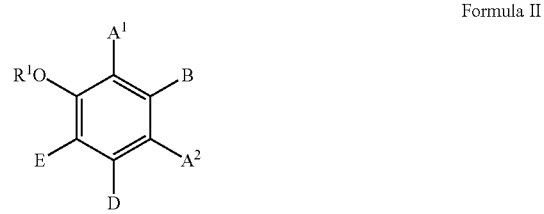

Formula II wherein R1 is hydrogen or methyl, A1 and A2 are the same or different and are selected from hydrogen, C1 to C12 linear or branched alkyl or alkenyl, C7 to C12 aralkyl or arylalkenyl which may have a substituent, C1 to C6 linear or branched alkoxy or alkenyloxy, halogen or —COR2 wherein R2 is selected from C1 to C12 linear or branched alkyl or alkenyl, C7 to C12 aralkyl or arylalkenyl which may have a substituent or C6 to C12 aromatic hydrocarbon which may have a substituent, B is selected form hydrogen, C1 to C12 linear or branched alkyl or alkenyl, C7 to C12 aralkyl or arylalkenyl which may have a substituent, —OR3 or —COOR3 wherein R3 is selected from hydrogen, C1 to C6 linear or branched alkyl or alkenyl, D is selected from hydrogen, hydroxyl, methyl or C1 to C12 linear or branched alkoxy or alkenyloxy, E is selected from hydrogen, hydroxyl or C1 to C6 linear or branched alkyl or alkenyl, or C1 to C6 linear or branched alkoxy or alkenyloxy, and two or three of A1, A2, B and E are hydrogen and the others are not containing sulfonic group, and wherein D is hydrogen or methyl, A1 and B or A2 and B may be bonded mutually to form a benzene ring which may have hydroxyl, with the condition that the composition does not comprise any compound of the general structure and/or a hydrate thereof and/or a salt thereof

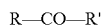

wherein R is selected from hydrogen, COOH, CN, optionally substituted $C_1$-$C_{10}$ alkyl, optionally substituted $C_2$-$C_{10}$ alkenyl, optionally substituted C2-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy and R' is COOH, d—increasing the temperature of the hair to a temperature in the range of 80 to 230° C. for 5 to 120 min, e—Optionally rinsing off the hair, f—Optionally blow drying the hair.

Another object of the present invention is a kit for hair comprising the aqueous composition as described above used in the process of the present invention.

In case that hair is given a curly shape, the hair is put on the curlers either before or after the step "c". The curlers are then taken off from hair after step "d" and prior to rinsing of the hair.

In a preferred embodiment of the present invention, the hair to be treated is dry and clean and therefore, prior to application of the aqueous composition onto hair in step c, hair, especially the dirty hair, is washed with a cleansing composition and dried. It should be noted that the treating humid, wet hair is not at all excluded from the scope of the invention. After the step d, preferably the hair is rinsed off with water and dried with a blow drier.

In a further preferred embodiment of the present invention, hair to be shaped is not treated with a reducing composition prior to semi permanently shaping with the present invention.

The process of the present invention does not involve reducing and oxidizing steps and therefore the composition used in the process is practically free of reducing agents. Therefore, the total concentration of reducing agents, if present, is less than 0.1% by weight, calculated to the total of the composition.

The hair is applied the aqueous composition comprising one or more compounds of the general structure according to Formula I and/or one or more compounds of the general structure of the Formula (II) above.

As the compounds represented by the formula I, a compound, wherein, in the above formula, $R^1$ and X are defined as those described above, $R^{x1}$ represents an aromatic hydrocarbon group, which is optionally substituted with up to three hydroxy groups or methoxy groups, and RY represents a hydrogen atom, a hydroxy group, a methoxy group, or an arylcarbonyloxy group or aralkylcarbonyloxy group, which is optionally substituted with up to three hydroxy groups or methoxy groups, is preferable.

Examples of the compounds corresponding to the Formula I include catechin, epicatechin, epigallocatechin, meciadanol, afzelechin, epiafzelechin, catechin gallate, epicatechin gallate, epigallocatechin gallate, phylloflavan, fisetinidol, guibourtinidol, and robinetinidol. The most preferred is Catechin.

The suitable compounds according to Formula (II) are resorcinol, 2-methyl resorcinol, 4-n-butyl resorcinol, 4-chlorresorcinol, resveratrol, phloretin and 2,2',4,4'-tetrahydroxybenzophenone. The most preferred is resorcinol.

In a preferred embodiment of the invention, the aqueous composition comprises only catechin.

The aqueous composition comprises one or more compounds of the Formula I and/or one or more compounds of the Formula II at a total concentration in the range of 1% to 50%, preferably 2% to 40%, more preferably 2.5% to 35% and even more preferably 4% to 30% by weight, calculated to the total of the aqueous composition.

The pH of the aqueous composition is in the range of 1.5 to 10, preferably 2 to 9, more preferably 4 to 8.

The aqueous composition comprises one or more alkalizing agents. Suitable ones are ammonia and alkyl- or alkanolamines according to the general structure

wherein $R_1$, $R_2$, and $R_3$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_1$, $R_2$, or $R_3$ is different from H, wherein the alkalizing agents preferably selected from ammonia, monoethanolamine, and aminomethyl-propanol, and particularly suitable one is aminomethyl-propanol.

The alkalizing agent is comprised in the aqueous composition at a total concentration of 0.1% to 10%, preferably 0.25% to 7.5%, more preferably 0.5% to 5% and most preferably 1% to 4% by weight calculated to the total of the aqueous composition.

The hair temperature is increased after application of the aqueous composition to a temperature in the range of 80 to 230° C., preferably in the range of 100 to 200° C., more preferably 110 to 180° C. and most preferably 120 to 180° C. Heating up the hair may be carried out with various tools such as irons, digital perming machine, in case curly hair is the target, which heats up the curlers and the heat is transferred to the hair. It has been observed that optimal and safe operation of the digital curling rods is achieved at a temperature 140° C.+/−10° C.

Although it may be possible to leave in the compositions applied onto hair and finishing the process without rinsing off the hair with water, rinsing off after finishing the obligatory treatment steps is preferred in order to maintain the natural cosmetic properties of hair, especially uncoated/unloaded feel and soft feeling upon touching.

In order to secure the optimal treatment, the hair is processed under elevated temperatures in an environment in which hair drying is prevented.

In a further embodiment of the present invention, the aqueous composition may comprise one or more thickening polymers selected from anionic, nonionic, cationic and amphoteric polymers, preferably selected from polymers with a viscosity of at least 500 mPa·s measured at a polymer concentration of 1% by weight in water and at 20° C. with a Brookfield viscometer, such as at 10 rpm for 1 min, with an appropriate spindle.

Suitable polymers are cellulose polymers, alginates, polysaccharides and acrylic acid polymers, preferably methyl cellulose, ethyl cellulose, hydroxyethylcellulose, methylhydroxyethylcellulose, methylhydroxypropylcellulose, carboxymethyl cellulose, alginic acids, sodium alginates, ammonium alginates, calcium alginates, gum arabic, guar gum or xanthan gum, dehydroxanthan gum or acrylic acid polymers known with the CTFA adopted name Carbomer and its derivatives.

The preferred polymers are hydroxyethylcellulose, dehydroxanthan gum, xanthan gum, guar gum and polymeric anionic thickeners Carbomer and its derivatives. The particularly preferred thickening agent is dehydroxanthan gum. The thickening agents are preferably comprised in the composition at a total concentration in the range of 0.1% to 2%, preferably, 0.2% to 1.75%, more preferably 0.25% to 1.5% and most preferably 0.3% to 1.25% by weight, calculated to the total of the aqueous composition. It should be noted that thickening is necessary in order to keep the aqueous compositions on the hair during their processing time.

The aqueous composition may comprise one or more of the commonly used hair conditioning compounds. These compounds are for example fatty alcohols, surfactants such as anionic, nonionic, cationic and amphoteric ones, ubiquinones, ceramides, organic solvents, lipophilic ingredients such as vegetable oils, mineral oils, silicones, fatty acid fatty alcohol esters, preservatives, amino acids, and polyols. It should be noted that these compounds are optionally comprised in the composition and their incompatibility must be carefully considered prior to addition into the composition.

The composition may comprise one or more fatty alcohols. In particular the compositions may further be in the form of an emulsion and then comprises preferably one or more fatty alcohols and one or more surfactants as emulsifier. Suitable fatty alcohols are the ones with the chain length of 14 to 22 C atoms which may be saturated or unsaturated, linear or branched which may as well be substituted. Non-limiting examples are myristyl alcohol, cetyl alcohol, stearyl alcohol, behenyl alcohol and cetostearyl alcohol. The total concentration of fatty alcohol is in the range from 0.1% to 7.5%, preferably 0.2% to 5% by weight, calculated to the total of the composition.

The surfactants suitable are selected from anionic, nonionic, amphoteric and/or cationic surfactants. The anionic, nonionic, amphoteric surfactants are used generally as emulsifier or solubilizer whereas the cationic surfactants are at the same time particularly used as hair conditioners.

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof as well as alkyl amido polyether carboxylic acids and salts thereof. Such products have been known for some time and are on the market, for example, under the trade name "AKYPO®" and "AKYPO-SOFT®".

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

Further suitable surfactants are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "Pluronics®", as well as fatty alcohol ethoxylates, $C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also been proven suitable.

Suitable cationic surfactants are according to the general structure

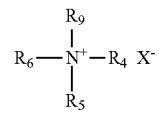

where $R_5$ is a saturated or unsaturated, branched or linear alkyl chain with 8-22 C atoms or

where $R_7$ is saturated or unsaturated, branched or linear alkyl chain with 7-21 C atoms and n has typical value of 1-4 or

where $R_8$ is saturated or unsaturated, branched or linear alkyl chain with 7-21 C atoms and n has typical value of 1-4, and $R_4$ is H or unsaturated or saturated, branched or linear alkyl chain with 1-22 C atoms or

or

where $R_7$, $R_8$ and n are same as above.

$R_9$ and $R_6$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

The concentration of total surfactants in the composition is in the range of 0.1% to 10%, preferably 0.2% to 7.5% and most preferably 0.2% to 5% by weight, calculated to the total of the composition.

The aqueous composition may further comprise lipophilic ingredients such as vegetable oils, for example, jojoba oil or any other natural oil; liquid paraffins, especially paraffinum perliquidum and parafiinum subliquidum, silicones for example linear polysiloxanes such as dimethicones with various consistency and dimethiconols, aminated silicones with secondary, tertiary or quaternary ammonium groups such as polysilicone 9, and quaternium 80, cyclic silicones such as cyclomethicones, arylated silicones such as phenyl trimethicone; fatty acid esters such as octyl palmitate, isocetyl palmitate, isopropyl palmitate and octyl stearate, $C_{10}$- to $C_{36}$-fatty acid triglycerides, as well as their mixtures. Total concentration of these lipophilic compounds is in the range of 0.1% to 20% by weight, preferably from 1% to 15% by weight, and more preferably from 2% to 10% by weight, calculated to the total of the composition.

The composition may also comprise cationic polymers as conditioning and/or thickening agents. Those are cationic cellulose type polymers know as Polymer JR type from Amerchol such as Polyquaternium 10 or cationic guar gum known with trade name Jaguar from Rhone-Poulenc and chemically for example Guar hydroxypropyl trimonium chloride. Furthermore, chitosan and chitin can also be included in the compositions as cationic natural polymers.

Furthermore, it has been found suitable to use those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

The composition may comprise one or more ceramide compound, such as the one according to general formula

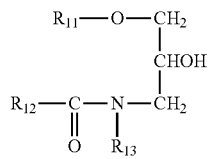

where $R_{11}$ and $R_{12}$ are independent from each other alkyl- or. alkenyl group with 10 to 22 carbon atoms, $R_{13}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01% to 2%, preferably 0.01% to 1% by weight calculated to the total of the composition.

The composition may comprise ubiquinone of the formula:

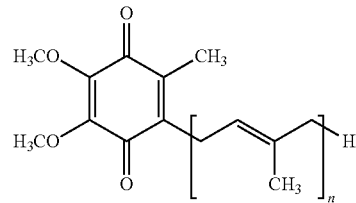

wherein n is a number from 1 to 10. The concentration of ubiquinone can vary between 0.001% and 10% by weight, calculated to the total of the composition.

The composition may comprise one or more organic solvent such as 2-phenoxyethanol, benzyl alcohol, 2-phenylethanol and 2-benzyloxyethanol. Suitable aliphatic alcohols are ethanol, isopropanol, propanol, n-butanol, isobutanol, t-butanol and 1-pentanol. Total concentration of one or more organic solvent is in the range of 1% to 50%, preferably 2% to 40% and more preferably 5% to 30% and most preferably 5% to 20% by weight calculated to the total of the composition.

The composition may further comprise one or more polyols, preferably at a concentration in the range of 0.01% to 5%, preferably 0.1% to 3% and more preferably 0.2% to 2.5% and most preferably 0.25% to 2% by weight calculated to the total of the composition. Suitable ones are propylene glycol, diproplylene glycol, glycerine, panthenol and its derivatives.

The compositions may further comprise any known preservatives if necessary, fragrance and any other cosmetically acceptable ingredient.

The following examples are to illustrate the invention but not to limit.

EXAMPLE 1

The following compositions were prepared and used in the tests in order to show the effect of the invention.

|  | Concentration % by weight | | | | |
|---|---|---|---|---|---|
|  | 1 | 2 | 3 | 4 | 5 |
| Catechin | 20 | 20 | 20 | 20 | 30 |
| Ammonia (25%) | — | 2 | 2 | 2 | 2 |
| Benzyl alcohol | 5 | 5 | — | — | — |
| Ethanol | — | — | 5 | — | — |
| Water | q.s. to 100 | | | | |
| pH | 4.0 | 8.4 | 8.4 | 8.4 | 8.4 |
| Processing temperature | 140 | 140 | 140 | 140 | 140 |
| Curl ratio % | 38 | 45 | 45 | 45 | 50 |

The above compositions were prepared and used for treating hair. Therefore, hair streaks with a length of 20 cm were used. The compositions were applied onto shampooed and dried hair in a hair to composition weight ratio of 1:1. Afterwards, the hair was put on rods of the digital perm machine and the rods were heated to 140° C. (measured on the hair with an infrared digital thermometer from a distance of 15 cm) and let on the hair for 30 min. The hair was covered with an aluminum sheet during processing in order to prevent hair drying. Afterwards the hair was taken off from the digital perming machine, rinsed off with water, blow dried, the length was measured and the curl ratio was calculated with the following equation.

Curl ratio $(CR) = ((L0-Lt)/L0) \times 100$

Wherein L0 is the length of the hair prior to the treatment, Lt is the length of the hair after the treatment.

From the above results it is clear that the hair is shaped with the process of the present invention.

Additionally, the curl durability of the hair streak obtained with the composition 3 of the above Table was tested by repeatedly washing the hair streak with a commercially available shampoo composition under the brand Goldwell. The following results were obtained.

| Number of wash cycles | Curl Ratio |
|---|---|
| Start | 45 |
| 5 | 30 |
| 10 | 16 |

Additionally, the tress treated with the composition 1 of the above Table, was straightened using a flat iron having a surface temperature of 230° C. The hair was treated 5 times with 3 sec heat application period and it was observed that the curly hair was straightened.

The same straightened hair was then again curled with curling iron operated at 180° C. for 30 sec and repeated 3 times the same and it was observed that the hair was curled again and had the similar curl retention value and similar wash fastness.

Similar results are observed with the following examples.

EXAMPLE 2

| | % by weight |
|---|---|
| Catechin | 20 |
| Polyquaternium-37 | 1 |
| Water | to 100 |

The above composition had a pH 4.0. The hair treated in the same way as describe above under Example 1 had the curl ratio of 60%.

EXAMPLE 3

| | % by weight |
|---|---|
| Catechin | 20 |
| Hydroxyethylcellulose | 1 |
| Water | to 100 |

The above composition had a pH 4.0. The hair treated in the same way as describe above under Example 1 had the curl ratio of 50%.

EXAMPLE 4

| | % by weight |
|---|---|
| Catechin | 20 |
| Xanthan gum | 1 |
| Water | to 100 |

The above composition had a pH 4.0. The hair treated in the same way as describe above under Example 1 had the curl ratio of 60%.

The invention claimed is:

1. A process for treating hair, the process comprising:
   a—optionally cleansing hair;
   b—optionally drying the hair;
   c—applying an aqueous composition onto hair, the aqueous composition comprising an alkalizing agent and one or more compounds of the general structure

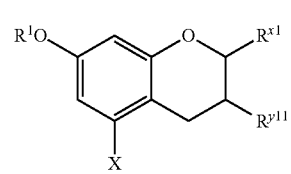

Formula I wherein
$R^1$ represents a hydrogen atom or a methyl group, X represents a hydrogen atom, a hydroxy group, or a methoxy group, $R^{x1}$ represents an aromatic hydrocarbon group, that is optionally substituted with up to three hydroxy groups or methoxy groups, and $R^{y11}$ represents a hydroxy group, a methoxy group, or an aromatic hydrocarbon group, that is optionally substituted with up to three hydroxy groups or methoxy groups or an arylcarbonyloxy group or aralkylcarbonyloxy group, that is optionally substituted with up to three hydroxy groups or methoxy groups, and/or

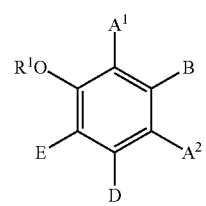

Formula II one or more compounds of the general structure
wherein $R^1$ is hydrogen or methyl, $A^1$ and $A^2$ are the same or different and are selected from hydrogen, C1 to C12 linear or branched alkyl or alkenyl, C7 to C12 aralkyl or arylalkenyl with or without a substituent, C1 to C6 linear or branched alkoxy or alkenyloxy, halogen or —COR2, B is selected from hydrogen, C1 to C12 linear or branched alkyl or alkenyl, C7 to C12 aralkyl or arylalkenyl with or without a substituent, —OR3 or —COOR3, D is selected from hydrogen, hydroxyl, methyl or C1 to C12 linear or branched alkoxy or alkenyloxy, E is selected from hydrogen, hydroxyl or C1 to C6 linear or branched alkyl or alkenyl, or C1 to C6 linear or branched alkoxy or alkenyloxy, and two or three of $A^1$, $A^2$, B and E are hydrogen and the others are not containing sulfonic group, and wherein D is hydrogen or methyl, $A^1$ and B or $A^2$ and B may be bonded mutually to form a benzene ring which may have hydroxyl, wherein the alkalizing agent is selected from ammonia and alkyl- or alkanolamines according to the general structure

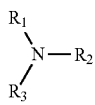

wherein $R_1$, $R_2$, and $R_3$ are the same or different and are selected from H, from C1 to C4, C3 to C4 unsaturated alkyl, C3 to C4 branched alkyl, C1 to C4 hydroxyl alkyl, C3 to C4 unsaturated hydroxyl alkyl, C3 to C4 branched hydroxyl alkyl, with the condition that at least one of $R_1$, $R_2$, or $R_3$ is different from H, wherein the aqueous composition comprises the one or more compounds of at least one selected from Formula I and Formula II at a total concentration in the range of 2 to 50% by weight, based on a total weight of the aqueous composition, with the condition that the aqueous composition does not comprise any compound of the general structure and/or a hydrate thereof and/or a salt thereof

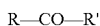

wherein R is selected from hydrogen, COOH, CN, optionally substituted C1-C10 alkyl, optionally substituted C2-C10 alkenyl, optionally substituted C2-C10 alkynyl, optionally substituted C3-C10 cycloalkyl, optionally substituted C6-C10 aryl or a 5-10-membered, optionally substituted heteroaryl group, wherein the optional substituents of the alkyl group are selected from halogen, hydroxyl, amino and C1-C4 alkoxy, and the optional substituents of the other groups are selected from halogen, hydroxyl, amino, C1-C4 alkyl and C1-C4 alkoxy and R' is COOH, and wherein the process is free from reducing and oxidizing steps;
d—increasing the temperature of the hair to a temperature in the range of 100 to 230° C. for 5 to 120 minutes;
e—optionally rinsing off the hair; and
f—optionally blow drying the hair.

2. The process according to claim 1, wherein the hair is put on curlers before or after the step c.

3. The process according to claim 2, wherein the curlers are taken off from hair after step d and prior to rinsing off the hair.

4. The process according to claim 1, wherein the hair is cleansed and dried prior to application of the aqueous composition in step c and rinsed off and blow dried after the step d.

5. The process according to claim 1, wherein the pH of the aqueous composition is in the range of 1.5 to 10.

6. The process according to claim 1, wherein the aqueous composition comprises the one or more compounds of at least one selected from Formula I and Formula II at a total concentration in the range of 2.5 to 40% by weight, based on the total weight of the aqueous composition.

7. The process according to claim 1, wherein at least one of
one or more compounds of formula I is at least one selected from the group consisting of catechin, epicatechin, epigallocatechin, meciadanol, afzelechin, epiafzelechin, catechin gallate, epicatechin gallate, epigallocatechin gallate, phylloflavan, fisetinidol, guibourtinidol, and robinetinidol, and
one or more compounds according to the Formula (II) is at least one selected from resorcinol, 2-methyl resorcinol, 4-n-butyl resorcinol, 4-chlorresorcinol, resveratrol, phloretin, and 2,2',4,4'-tetrahydroxybenzophenone.

8. The process according to claim 1, wherein the one or more compounds of the general structure according to Formula I consists of catechin.

9. The process according to claim 1, wherein the aqueous composition comprises one or more thickening polymers selected from anionic, nonionic, cationic and amphoteric polymers, selected from polymers with a viscosity of at least 500 mPa s measured at a polymer concentration of 1% by weight in water and at 20° C. with a Brookfield viscometer, at 10 rpm for 1 minute, with an appropriate spindle, selected from cellulose polymers, alginates, polysaccharides and acrylic acid polymers, methyl cellulose, ethyl cellulose, hydroxyethylcellulose, methylhydroxyethylcellulose, methylhydroxypropylcellulose, carboxymethyl cellulose, alginic acids, sodium alginates, ammonium alginates, calcium alginates, gum arabic, guar gum or xanthan gum, dehydroxanthan gum or acrylic acid polymers known with the CTFA adopted name Carbomer and its derivatives, comprised in the compositions at a total concentration in the range of 0.1% to 2% by weight, based on the total weight of the aqueous composition.

10. The process according to claim 1, wherein the aqueous composition comprises one or more organic solvent, at a total concentration in the range of 1% to 50% by weight, based on the total weight of the aqueous composition, selected from 2-phenoxyethanol, benzyl alcohol, 2-phenylethanol, 2-benzyloxyethanol, ethanol, isopropanol, propanol, n-butanol, isobutanol, t-butanol, and 1-pentanol.

11. The process according to claim 1, wherein the aqueous composition comprises:
one or more hair conditioning compounds;
one or more fatty alcohols;
one or more surfactants selected from anionic surfactants, nonionic surfactants, cationic surfactants, and amphoteric surfactants;
one or more ubiquinones;
one or more ceramides;
one or more organic solvents;
one or more lipophilic ingredients selected from one or more vegetable oils,
one or more mineral oils, one or more silicones, and fatty acid esters;
one or more preservatives;
one or more amino acids; and
one or more polyols.

12. The process according to claim 1, wherein the alkalizing agents are selected from ammonia, monoethanolamine, and aminomethyl-propanol and are present at a total concentration in the range of 1 to 4% by weight, based on the total weight of the aqueous composition.

13. The process according to claim 5, wherein the pH of the aqueous composition is in the range of 2 to 9.

14. A process for treating hair, the process comprising:
a—optionally cleansing hair;
b—optionally drying the hair;
c—applying an aqueous composition onto hair comprising one or more compounds of the general structure

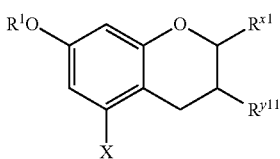

Formula I wherein
R¹ represents a hydrogen atom or a methyl group,
X represents a hydrogen atom, a hydroxy group, or a methoxy group,
$R^{x1}$ represents an aromatic hydrocarbon group, that is optionally substituted with up to three hydroxy groups or methoxy groups, and
$R^{y11}$ represents a hydroxy group, a methoxy group, or an aromatic hydrocarbon group, that is optionally substituted with up to three hydroxy groups or methoxy groups or an arylcarbonyloxy group or aralkylcarbonyloxy group, that is optionally substituted with up to three hydroxy groups or methoxy groups,
wherein the aqueous composition comprises the one or more compounds of Formula I at a total concentration in the range of 20 to 50% by weight, based on
a total weight of the aqueous composition,
with the condition that the aqueous composition does not comprise any compound of the general structure and/or a hydrate thereof and/or a salt thereof

R—CO—R' wherein R is selected from hydrogen, COOH, CN, optionally substituted C1-C10 alkyl, optionally substituted C2-C10 alkenyl, optionally substituted C2-C10 alkynyl, optionally substituted C3-C10 cycloalkyl, optionally substituted C6-C10 aryl or a 5-10-membered, optionally substituted heteroaryl group, wherein the optional substituents of the alkyl group are selected from halogen, hydroxyl, amino and C1-C4 alkoxy, and the optional substituents of the other groups are selected from halogen, hydroxyl, amino, C1-C4 alkyl and C1-C4 alkoxy and R' is COOH;
d—increasing the temperature of the hair to a temperature in the range of 80 to 230° C. for 5 to 120 minutes;
e—optionally rinsing off the hair; and
f—optionally blow drying the hair.
15. A process for treating hair, the process comprising:
a—optionally cleansing hair;
b—optionally drying the hair;
c—applying an aqueous composition onto hair comprising one or more compounds of the general structure

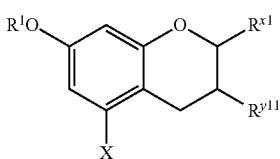

Formula I wherein
R¹ represents a hydrogen atom or a methyl group,
X represents a hydrogen atom, a hydroxy group, or a methoxy group,
$R^{x1}$ represents an aromatic hydrocarbon group, that is optionally substituted with up to three hydroxy groups or methoxy groups, and
$R^{y11}$ represents a hydroxy group, a methoxy group, or an aromatic hydrocarbon group, that is optionally substituted with up to three hydroxy groups or methoxy groups or an arylcarbonyloxy group or aralkylcarbonyloxy group, that is optionally substituted with up to three hydroxy groups or methoxy groups,
and/or one or more compounds of the general structure

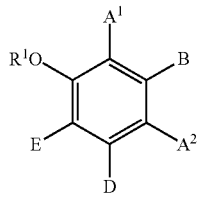

Formula II wherein R¹ is hydrogen or methyl, A¹ and A² are the same or different and are selected from hydrogen, C1 to C12 linear or branched alkyl or alkenyl, C7 to C12 aralkyl or arylalkenyl with or without a substituent, C1 to C6 linear or branched alkoxy or alkenyloxy, halogen or —COR2, B is selected from hydrogen, C1 to C12 linear or branched alkyl or alkenyl, C7 to C12 aralkyl or arylalkenyl with or without a substituent, —OR3 or —COOR3, D is selected from hydrogen, hydroxyl, methyl or C1 to C12 linear or branched alkoxy or alkenyloxy, E is selected from hydrogen, hydroxyl or C1 to C6 linear or branched alkyl or alkenyl, or C1 to C6 linear or branched alkoxy or alkenyloxy, and two or three of A¹, A², B and E are hydrogen and the others are not containing sulfonic group, and wherein D is hydrogen or methyl, A¹ and B or A² and B may be bonded mutually to form a benzene ring which may have hydroxyl,
wherein the aqueous composition comprises the one or more compounds of at least one selected from Formula I and Formula II at a total concentration in the range of 2 to 50% by weight, based on a total weight of the aqueous composition,
with the condition that the aqueous composition does not comprise any compound of the general structure and/or a hydrate thereof and/or a salt thereof

R—CO—R' wherein R is selected from hydrogen, COOH, CN, optionally substituted C1-C10 alkyl, optionally substituted C2-C10 alkenyl, optionally substituted C2-C10 alkynyl, optionally substituted C3-C10 cycloalkyl, optionally substituted C6-C10 aryl or a 5-10-membered, optionally substituted heteroaryl group, wherein the optional substituents of the alkyl group are selected from halogen, hydroxyl, amino and C1-C4 alkoxy, and the optional substituents of the other groups are selected from halogen, hydroxyl, amino, C1-C4 alkyl and C1-C4 alkoxy and R' is COOH, and
wherein a total reducing agent concentration in the aqueous composition is less than 0.1% by weight, calculated to the total weight of the aqueous composition;
d—increasing the temperature of the hair to a temperature in the range of 110 to 230° C. for 5 to 120 minutes with a hair style tool selected from the group consisting of a flat iron, a curling iron, one or more curlers, one or more digital curling rods, and one or more rods of a digital perm machine;
e—optionally rinsing off the hair; and
f—optionally blow drying the hair.

* * * * *